(12) United States Patent
Hill et al.

(10) Patent No.: US 11,860,145 B2
(45) Date of Patent: Jan. 2, 2024

(54) SYSTEMS AND METHODS FOR AUTOMATED WETSTOCK MANAGEMENT

(71) Applicant: Wayne Fueling Systems LLC, Austin, TX (US)

(72) Inventors: Philip Hill, Skelmersdale (GB); Prem Swaroop, Watertown, MA (US); Atish Kamble, Watertown, MA (US); Konstantin Streltsov, Cracow (PL); Krystian Kulig, Cracow (PL)

(73) Assignee: Wayne Fueling Systems LLC, Austin, TX (US)

( * ) Notice: Subject to any disclaimer, the term of this patent is extended or adjusted under 35 U.S.C. 154(b) by 0 days.

(21) Appl. No.: 18/123,677

(22) Filed: Mar. 20, 2023

(65) Prior Publication Data

US 2023/0230034 A1    Jul. 20, 2023

Related U.S. Application Data

(63) Continuation of application No. 16/506,614, filed on Jul. 9, 2019, now Pat. No. 11,619,620.

(51) Int. Cl.
| | |
|---|---|
| *G01N 33/22* | (2006.01) |
| *G01F 1/00* | (2022.01) |
| *G05B 13/02* | (2006.01) |
| *G05B 13/04* | (2006.01) |
| *G06Q 10/0635* | (2023.01) |
| *G08B 21/18* | (2006.01) |
| *G01F 23/80* | (2022.01) |
| *G06Q 10/087* | (2023.01) |

(Continued)

(52) U.S. Cl.
CPC .............. *G01N 33/22* (2013.01); *B67D 7/32* (2013.01); *B67D 7/78* (2013.01); *G01F 1/007* (2013.01); *G01F 23/80* (2022.01); *G05B 13/0265* (2013.01); *G05B 13/04* (2013.01); *G06Q 10/0635* (2013.01); *G06Q 10/087* (2013.01); *G08B 21/182* (2013.01)

(58) Field of Classification Search
CPC .. G01N 33/22; G06Q 10/0635; G06Q 10/087; B67D 7/32; B67D 7/3209; B67D 7/362; B67D 7/78
See application file for complete search history.

(56) References Cited

U.S. PATENT DOCUMENTS

2017/0205268 A1* 7/2017 Misson ................. G01F 23/804

* cited by examiner

*Primary Examiner* — Benyam Haile
(74) *Attorney, Agent, or Firm* — Mintz Levin Cohn Ferris Glovsky and Popeo, P.C.

(57) ABSTRACT

An automated wetstock management system can include a plurality of sensors disposed in a fuel storage facility, the plurality of sensors configured to sense fuel data characterizing one or more aspects of the fuel storage facility, and a wetstock management server communicatively coupled to the plurality of sensors. The wetstock management server can process the fuel data to detect whether the fuel data satisfies an exception indicative of an operational issue of the fuel storage facility based on one or more predefined rules or models stored in the wetstock management server. In some embodiments, the wetstock management server can generate a workflow for assisting a user of the fuel storage facility to resolve the operational issue. In some embodiments, the wetstock management server can assign a risk category to the exception and electronically transmit an alert characterizing the operational issue to the user.

15 Claims, 3 Drawing Sheets

(51) Int. Cl.
*B67D 7/78* (2010.01)
*B67D 7/32* (2010.01)

SYSTEMS AND METHODS FOR AUTOMATED WETSTOCK MANAGEMENT

CROSS REFERENCE TO RELATED APPLICATIONS

This application is a continuation of U.S. patent application Ser. No. 16/506,614, filed Jul. 9, 2019 and entitled "SYSTEMS AND METHODS FOR AUTOMATED WETSTOCK MANAGEMENT," the entire contents of which are hereby expressly incorporated by reference herein.

FIELD

Systems and methods are provided for automated management of wetstock.

BACKGROUND

Wetstock management is an essential function in day-to-day operations of a fuel storage facility. Typically, wetstock management can involve the monitoring of fuel stock at a fuel storage facility using a variety of measurement devices, such as automatic tank gauges (ATGs), fuel leak detection sensors, magnetostrictive probes, and so forth, evaluating measurements to detect abnormal, and often unsafe, events affecting the fuel stock (e.g., fuel losses, fuel excesses, tank defects, operational issues, etc.), and performing corrective actions as necessary.

Traditionally, wetstock measurements can be evaluated manually by a storage facility operator. The operator can be responsible for monitoring the measurements in order to identify anomalies and respond appropriately. However, the practice of relying upon humans to manually monitor large volumes of sensor data can be error prone, potentially resulting in the failure to detect and resolve problems at an early stage. Such failure, in the context of wetstock management, could produce catastrophic consequences such as environmental contamination, loss of revenue, damaged reputation, and public health risks.

SUMMARY

Methods and devices are provided for automated wetstock management. In one exemplary embodiment, one or more of a plurality of sensors disposed in a fuel storage facility can sense fuel data characterizing one or more aspects of the fuel storage facility. A wetstock management server, which is communicatively coupled to the plurality of sensors, can process the fuel data to detect whether the fuel data satisfies an exception indicative of an operational issue of the fuel storage facility based on one or more predefined rules or models stored in the wetstock management server.

In certain exemplary embodiments, the wetstock management server can identify an operational issue of the fuel storage facility based on the exception when said exception is detected. The wetstock management server can then automatically generate a workflow including a series of steps for assisting one or more users of the fuel storage facility to resolve the identified operational issue. Furthermore, a device communicatively coupled to the wetstock management server can display a visual characterization of the workflow using a display unit of the device In certain exemplary embodiments, the wetstock management server can assign a risk category among a plurality of predefined risk categories to the exception based on one or more exception criteria associated with each of the plurality of predefined risk categories when said exception is detected. Based on the identified risk category, the wetstock management server can automatically select one or more electronic communication channels and electronically transmit an alert characterizing the operational issue to the one or more users via the one or more selected electronic communication channels.

BRIEF DESCRIPTION OF THE DRAWINGS

The embodiments herein may be better understood by referring to the following description in conjunction with the accompanying drawings in which like reference numerals indicate identically or functionally similar elements, of which.

It should be understood that the above-referenced drawings are not necessarily to scale, presenting a somewhat simplified representation of various preferred features illustrative of the basic principles of the disclosure. The specific design features of the present disclosure, including, for example, specific dimensions, orientations, locations, and shapes, will be determined in part by the particular intended application and use environment.

DETAILED DESCRIPTION

Wetstock management can involve the usage of fuel data sensors to monitor the fuel stock at a fuel storage facility, evaluating measurement data to detect anomalies affecting the fuel stock, and performing corrective actions as necessary. The sensors can measure fuel data characterizing myriad possible aspects of the fuel storage facility. For example, fuel losses due to leaks, theft, delivery shortages, or the like can be detected and damage to storage equipment can be identified. By automating these processes in a "smart" manner applying, for instance, artificial intelligence and/or machine learning techniques, as described below, wetstock management can be performed more efficiently, economically, and safely.

Embodiments of methods and systems for automated wetstock management are discussed herein below.

Figure 1:
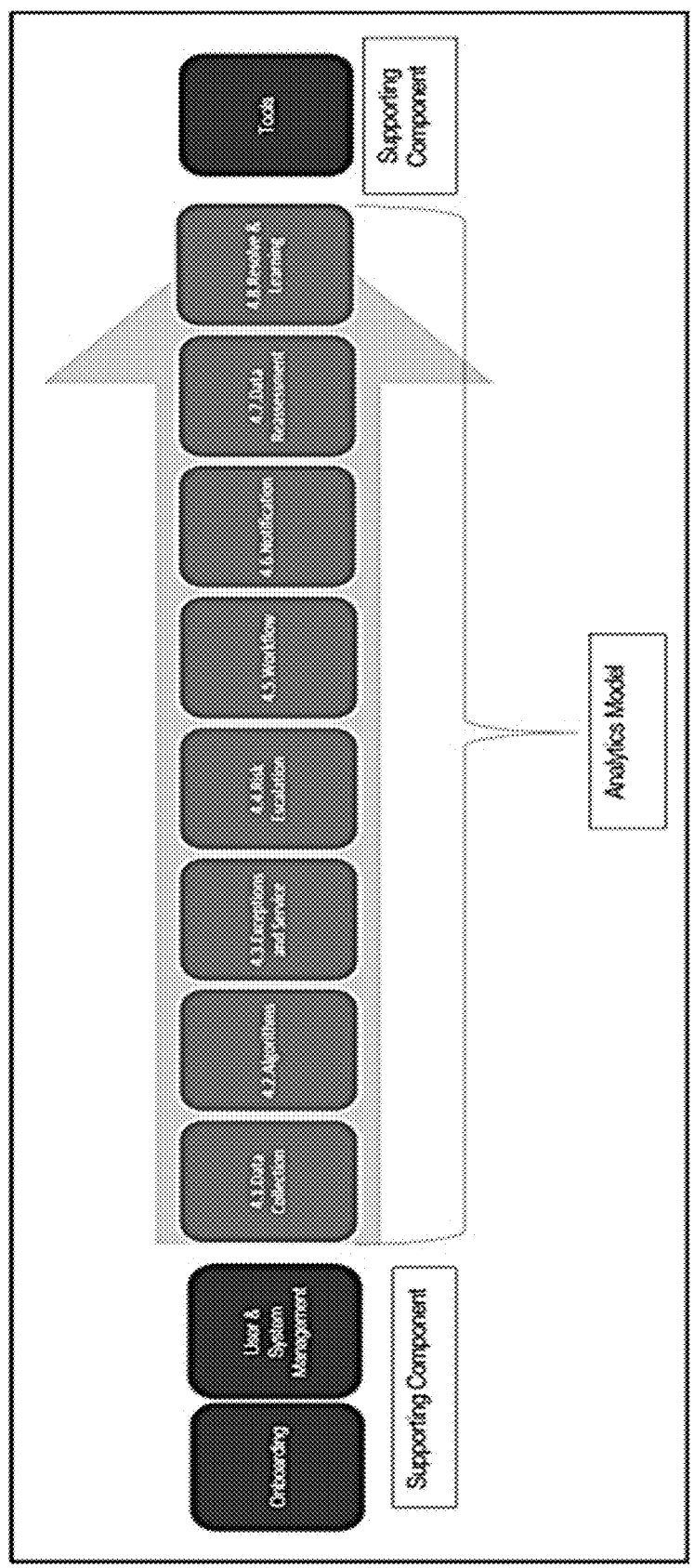
FIG. 1 is a flowchart illustrating an exemplary overview of an automated wetstock management system.

FIG. 1 illustrates one embodiment of an exemplary automated wetstock management system. The automated wetstock management system ("wetstock system") 100 can provide an automated, alert-driven wetstock management service using automated processing, artificial intelligence, and/or machine learning technologies to dynamically create workflows for the purpose of resolving issues arising in a given fuel storage facility. In some embodiments, operation of the wetstock system 100 can be carried out by a remote, cloud-based wetstock management server (not shown) configured to perform one or more operations described below. The wetstock system 100 can collect electronic fuel data characterizing one or more aspects of the fuel storage facility including, but not limited to, fuel stored in the facility, storage equipment (e.g., tanks), monitoring equipment, etc., from multiple sources such as, for example, automatic tank gauges (ATGs), point of sale devices, forecourt controllers, back office systems, fuel dispensers, and the like, as well as manually submitted fuel data (e.g., through a wetstock management computer application, website, etc.). The wetstock system 100 can process the collected data automatically through various algorithms, machine learning, and/or artificial intelligence to create alerts and/or exceptions.

Additionally, the wetstock system 100 can apply risk categorization to a dynamically created diagnostic workflow. The wetstock system 100 can evaluate incoming data when an exception is raised, validate the exception to filter out any invalid exceptions, categorize the exception based on risk, identify the most likely fault, as well as the probability of said fault, and notify a user (e.g., fuel storage facility operator or manager, fuel merchant, etc.) in a bespoke manner. In addition to exception-specific faults, the wetstock system 100 can utilize the individual exceptions to generate a consolidated risk-versus-probability model and solution. Finally, resolved issues can be tracked and logged by the wetstock system 100. The data can used as training data in a machine learning context to enable the wetstock system 100 to learn from previous diagnoses and more effectively diagnose similar situations in the future.

According to some embodiments, as shown in FIG. 1, the wetstock system 100 can be configured to embody a supporting component 110 and an analytics component 120, each of which composed of multiple individual elements. However, the wetstock system 100 is not limited solely to such configuration. The supporting component 110 of the wetstock system 100 can include the components necessary to enable an analytics model, implemented by the analytics component 120 to function and be serviced. The analytics component 120 of the wetstock system 100 can include the components according to which collected fuel data is processed and analyzed. It is understood that the supporting and analytics components 110 and 120 are not limited solely to the configurations shown in FIG. 1 and described below, but can be re-configured and/or re-arranged in any suitable manner, as would be understood by a person of ordinary skill in the art, consistent with the scope of the present claims defined herein.

Operationally, the wetstock system 100 can execute individual units of the supporting and analytics components 110 and 120 in a particular order, such as the order depicted in FIG. 1. However, the ordering of units shown in FIG. 1 is provided merely for demonstration purposes, and operation of the wetstock system 100 is not limited solely thereto. Thus, units of the supporting and analytics components 110 and 120, respectively, can be executed in any suitable order, as would be understood by a person of ordinary skill in the art, consistent with the scope of the present claims defined herein.

Referring now to FIG. 1, the supporting component 110 can initialize the wetstock system 100 by executing units that support or enable operation of the analytics component 120 whereby the collected fuel data is automatically processed and analyzed. Firstly, for example, an onboarding unit 111 can be executed whereby features required to initialize organizations, sites, wetstock details, and the like are carried out. Similarly, a user and system management unit 112 can be performed whereby features required to initialize one or more users (e.g., fuel storage facility operator or manager, fuel merchant, etc.) of the wetstock system 100 are carried out. For example, one or more registered users of the wetstock system 100 can be loaded, preferences of the one or more users can be imported, user permissions can be set, and so forth. In addition, features required to initialize the wetstock system 100 itself can be executed. For example, security settings, site groups, and the like associated with the wetstock system 100 can be initialized. The user and system management unit 112 can initialize user and system settings using operation data stored in a local or remote memory (not shown), depending on the configuration, characterizing one or more aspects of previous operations of the wetstock system 100. In cases where said operation data does not exist, the user and system management unit 112 can initialize user and system settings according to a default configuration.

Once the supporting component 110 has initialized the wetstock system 100 by executing units that support or enable operation of the analytics component 120, units of the analytics component 120 can be executed. Firstly, for example, a data processing unit 121, which encompasses both the import and export of data, can be performed. In detail, the data processing unit 121 can begin by collecting fuel data characterizing one or more aspects of a fuel storage facility from a wide variety of devices such as sensors or other measurement tools. These devices can include, for example, ATGs, fuel leak detection sensors, magnetostrictive probes, point of sale devices, forecourt controllers, back office systems, fuel dispensers, and so on. Also, users of the wetstock system 100 can manually submit data to be processed. All inputted data can be combined and exported for automated evaluation using predefined algorithms (122) of the wetstock system 100.

An algorithms unit 122 can then be executed whereby the fuel data collected in the data processing unit 121 is inputted to one or more predefined models and/or rules of the wetstock system 100. Algorithms of the wetstock system 100 can include any models and/or rules for processing the collected fuel data to generate one or more exceptions (123) when said one or more exceptions exist. The algorithms can be used to evaluate the collected input data for myriad purposes such as analyzing fuel loss, flow rates, delivery yields, etc., in order to alert the user of any issues occurring in the fuel storage facility. Such algorithms can encompass, but are not limited to, anomaly detection (e.g., detecting the presence of a value outside of a calculated or pre-configured normal range for a value during a given time slice), trend analysis (e.g., detecting the tendency of a value to move toward a range considered to be unacceptable), cross-value correlation (e.g., detecting the tendency of a value to change based on values of another variable or external events), and so on. To these ends, the input data can be analyzed in various ways such as calculating a maximum or minimum value over a given time slice, calculating an average, mean, or median value over a given time slice, calculating a standard deviation over a given time slice, and so on. For example, an average value in a given time slice (e.g., week, month, quarter, year, etc.) can be compared with a corresponding average value associated with a past time slice to detect anomalies. In some embodiments, multiple algorithms can be combined to create new algorithms. Output data generated by execution of these algorithms can be used to identify exceptions, escalate risk, and/or apply to further algorithms.

Next, an exceptions and services unit 123 can be executed whereby exceptions generated through the processing of collected fuel data via the algorithms described above can be delivered to the user. For the purpose of the present disclosure, an exception can refer to any data outputted via the algorithms unit 122 having a value which is outside of a predefined normal, or safe, range or threshold. For example, a fuel leak can cause a sudden decrease in fuel tank level. If an ATG detects that said level is less than a predefined minimum tank level threshold, an exception indicative of a fuel leak can be present. A wide range of services can be provided to the user based on the generated exceptions including, for example, predictive maintenance of impending faulty equipment, regulatory report generation and delivery to the appropriate standards bodies, authority notification when product theft is detected, predictive delivery of product based on trends, vendor notification of incorrect delivery of product (e.g., insufficient delivery, incorrect product, etc.), automated shutdown of fuel pumps due to detected issues (e.g., leaks, mechanical pump issues, etc.), and so on.

Next, a risk escalation unit 124 can be executed whereby a risk category can be assigned to an exception generated through the algorithms unit 122 and exceptions and services unit 123 based on a variety of factors. The risk assignment can be used to determine whether or not to escalate the exception, as well as the extent to which the exception is escalated. Moreover, risk categorization can allow users to assign rules to a particular risk category that is specific to their needs. In some cases, as anomalies in the input data are detected and exceptions are generated in the manner described above, a machine learning-based system can examine the actions taken to address an anomalous situation, such as a fuel leak, as it occurs in real-time. Thus, when the exception re-occurs, the response time can be compared against both configured service level agreements and past resolutions to determine whether the correct resources are being applied and the appropriate attention is being given to the fuel leak. Further, as new anomalies in the fuel data are detected, and exceptions are generated which can exacerbate the situation, machine learning techniques can use the past resolutions as training data to change the resources assigned or invoke automated reactions to a new higher or lower risk. Examples of these reactions could be shutting down devices, notifying the authorities, notifying more experienced personnel, and so on.

Next, a workflow unit 125 can be executed whereby a workflow including a series of steps for assisting the user to resolve an identified operational issue can be generated in real-time based on an identified exception and the risk category assigned thereto. The workflow can provide end-to-end support for the user to resolve an operational issue in the most appropriate and efficient manner, taking into account on-site equipment, depending on the threat and seriousness of the issue. For example, when the operational issue is a fuel leak, the workflow can include steps intended to correct or prevent exacerbation of the fuel leak. The workflow can be provided to the user in a manner determined according to the generated exception and the level of risk assigned thereto. In some embodiments, a device (e.g., a computing device such as a computer, mobile device, tablet device, etc.) coupled to a wetstock management server (not shown) responsible for performing elements of the analytics component 120 can display a visual characterization of the workflow, via a display unit of the device, enabling the user to read and follow the displayed workflow steps.

Next, a notifications unit 126 can be executed whereby a notification or alert, each of which is used interchangeably herein, characterizing the operational issue can be generated and sent to the user through a variety of possible communication channels or mechanisms. The notifications can be generated to allow for specific messages and channels of communications to be used depending on the type of alert. Multiple different users can be notified at a time which can vary based on the time of day. Also, the notification can be created and transmitted in a manner determined based on the assigned risk category, such that users are alerted only to on-site equipment issue when certain rules and/or risks are breached.

Upon resolution of the operational issue, e.g., a detected fuel leak has been eliminated, a data reassessment unit 127, a resolve and learning unit 128, and a tools unit 113 can be executed, thereby completing the analytics component 120 and the supporting component 110 for the particular exception. The assigned risk category can be de-escalated in response to issue resolution, but the fuel data can still be collected and monitored to ensure the exception no longer occurs. Moreover, the wetstock system 100 can maintain records for continual improvement thereof, such as validation of the workflow and training of models. In this regard, machine learning techniques can be applied to train rules, thresholds, and/or settings, using available information (e.g., collected fuel data, generated exception, workflow, notifications, etc.) as input. As a result, the workflows and notifications provided through the wetstock system 100 in response to exceptions can improve throughout the operational lifespan of the system.

As an illustrative example, it is assumed that a fuel storage facility is equipped with a tank overfill alarm that activates when an ATG coupled to a fuel tank detects a particular stock level volume. A fuel data collection device (not shown), such as an Internet of Things (IoT) device, located on-site can collect the ATG data and transmit the collected data to a remotely located wetstock management server (not shown) configured to perform operations of the wetstock system 100. Particularly, the wetstock management server can execute the aforementioned units of the analytics components 120 including the data processing unit 121 to collect the ATG data from the fuel data collection device in conjunction with fuel data measured by other on-site devices and/or manually inputted data, the algorithms unit 122 to process the collected data according to one or more predefined rules and/or models, the exceptions and services unit 123 to determine whether an exception, e.g., a fuel tank level outside of a safe range, exists, the risk escalation unit 124 to assign a detected exception a risk category, and the workflow unit 125 to generate a workflow providing end-to-end support for the user to resolve the issue causing the exception.

The wetstock management server can further execute the notifications unit 126 to determine a notifying action dependent upon user-specific and tank-specific settings. In some cases, multiple risk categories each of which corresponding to one or more predefined exception criteria can be created. Each risk category can also correspond to one or more channels of electronic communication through which a notification is to be delivered, such as an automated phone call, short message service (SMS) message (text message), e-mail, push notification to wetstock management application, and so on. As the risk category increases in urgency, more communication channels can be selected for transmission of the notification. A risk category among the plurality of possible risk categories can be assigned to the exception based upon the exception criteria(s) associated with each risk category. For illustration, an example set of risk categories and corresponding criteria and communication channel is provided below in Table 1.

TABLE 1

| Risk Category Type | Exception Criteria | Communication Channel |
|---|---|---|
| Risk Category 1 | Nominal capacity has been equaled or exceeded | Phone call; SMS; E-mail; Push notification |
| Risk Category 2 | Safe working capacity (SWC) has been breached by more than 100 liters | SMS; Push notification |
| Risk Category 3 | SWC has been breached by less than 100 liters | Push notification |
| Risk Category 4 | SWC has not been breached | No alert |

Based on the risk category of the generated exception, a notification describing the operational issue can be generated and electronically transmitted via the corresponding electronic communication channel(s). The notification can include any available data characterizing the nature of the issue. As the risk of the operational issue, e.g., the severity of the fuel leak, increases, so too does the number of communication channels through which the notification is transmitted. The day and time of the detected operational issue can determine the user or users that are notified.

The notified user(s) can then log on to an application of the wetstock system 100 and review the workflow generated by the wetstock management server for the exception that will guide them through resolving the issue (e.g., fuel leak). The workflow can include recommendations such as checking particular locations, e.g., interceptors, forecourt sensors, etc., for signs of fuel spills, contacting relevant authorities or response teams, and so on. After the issue has been resolved, the wetstock system 100 can maintain records for learning purposes so that in the event of a future stock reading at the same height, the risk of such issue is already known and can be more efficiently addressed.

Figure 2:
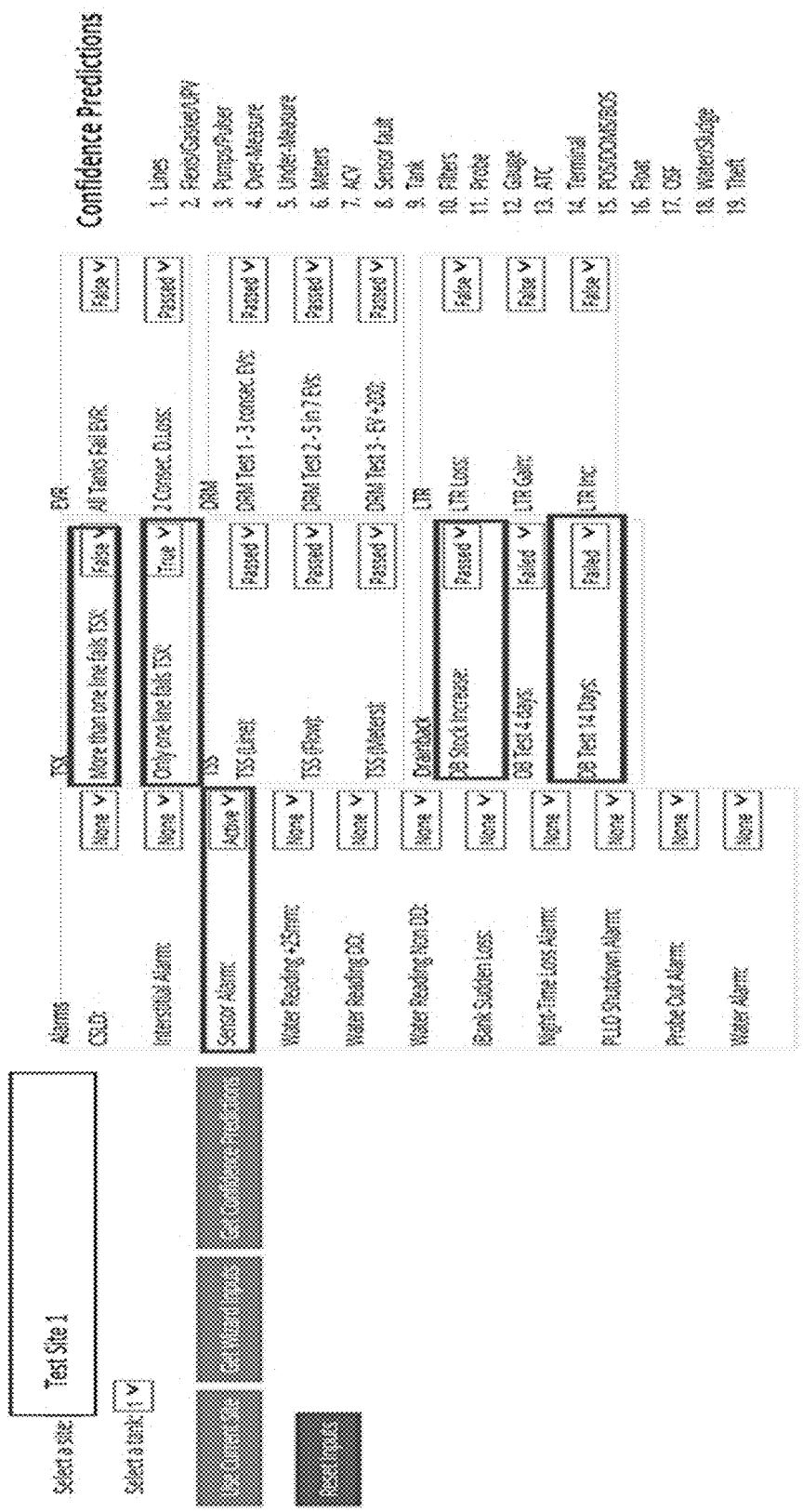
FIG. 2 is an exemplary user interface implemented by the automated wetstock management system of FIG. 1.

The wetstock system 100 can implement a wetstock management computer application with a user interface through which the user can interact with the wetstock system 100 by viewing workflows, receiving notifications (e.g., push notifications), and the like. In this regard, FIG. 2 is an exemplary user interface implemented by the wetstock system 100. The user interface 200 can include a variety of interactive elements intended to inform the user of information characterizing one or more aspects of the fuel storage facility provided by the wetstock system 100. For example, the user interface 200 can include a test site selection section 210 in which the user can select a test site of the fuel storage facility (e.g., Test Site 1), as well as a particular tank (e.g., Tank 1) of the selected site. The test site selection section 210 can also include selectable elements (e.g., buttons, drop-down menus, test input bars, etc.) enabling the user to quickly select a current site, receive confidence predictions (described below), and/or reset all input data collected by the wetstock system 100.

Additionally, the user interface 200 can include a fuel data section 220 displaying information based on collected fuel data characterizing one or more aspects of the fuel storage facility. For example, the fuel data section 220 can include status indicators of sensors, alarms, and so forth within the fuel storage facility. Moreover, the fuel data section 220 can include visual indicators of both active and inactive exceptions as determined automatically by the wetstock system 100 based upon the collected fuel data. As shown in FIG. 2, the fuel data objects 221 can indicate inactive exceptions, while the fuel data objects 222 can indicate active exceptions. As such, the wetstock system 100 is not limited to recognizing only a single exception at a time, but can recognize multiple exceptions under certain circumstances.

In some embodiments, the wetstock system 100 can combine the multiple exceptions as indicated by fuel data objects 221 and 222 in order to predict the most likely cause of the exceptions. In this regard, the user interface 200 can include a confidence prediction section 230 in which one or more possible faults are provided in order of probability calculated using wetstock system 100 analytics described above. As shown in FIG. 2, for example, a line issue can be predicted as the most likely fault or cause of the current exceptions. Based upon the predicted most likely fault, the wetstock system 100 can generate a workflow in the manner described above, which can be displayed for the user through the user interface 200. In some embodiments, the user can select a particular predicted cause of the exceptions, and the workflow can be generated based upon the selected cause.

Figure 3:
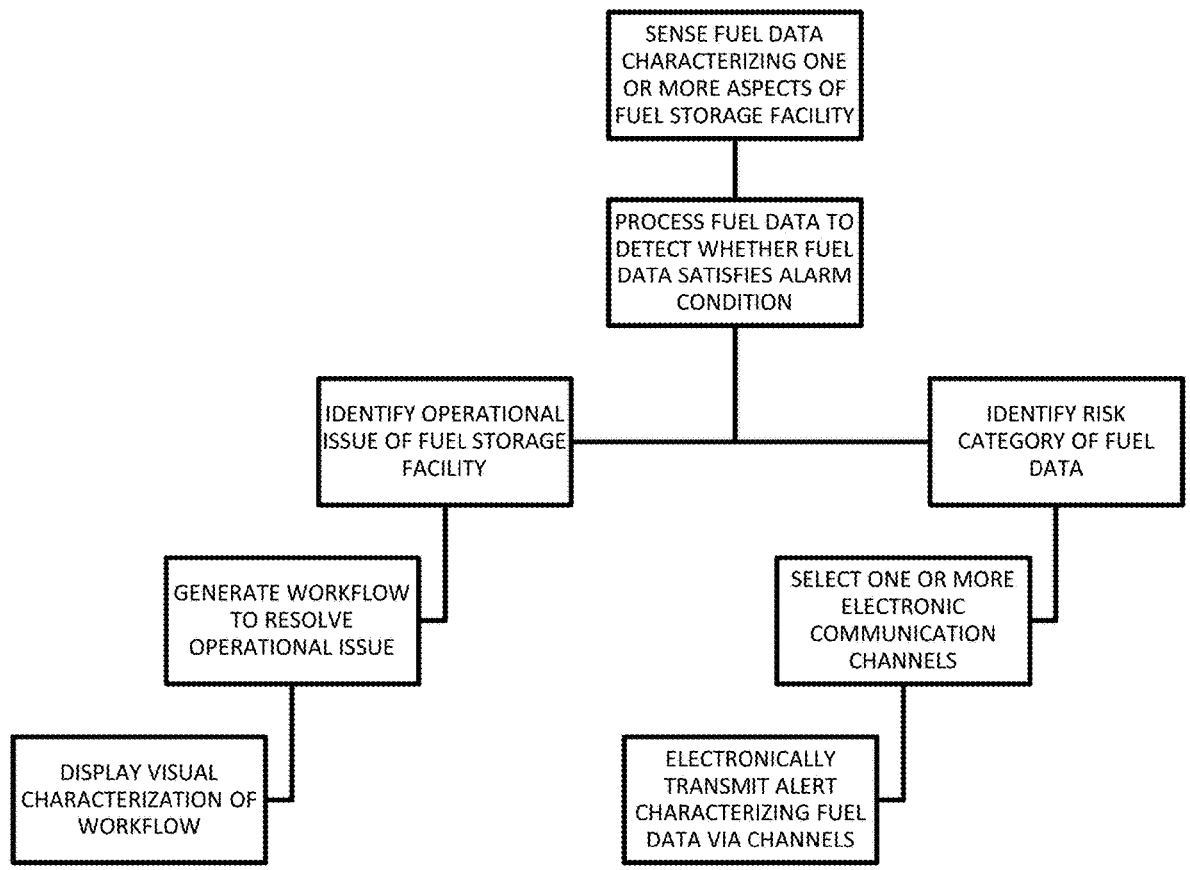
FIG. 3 is a flowchart illustrating an exemplary, simplified procedure implemented by the automated wetstock management system of FIG. 1.

FIG. 3 is a flowchart illustrating an exemplary, simplified procedure implemented by the wetstock system 100. The procedure 300 can start at step 305, and continue to step 310, where, as described in greater detail below, the wetstock system 100 can perform automated wetstock management to enable resolution of exceptions identified during operation of a fuel storage facility.

At step 305, one or more sensors of a plurality of sensors (e.g., ATGs, fuel leak detection sensors, magnetostrictive probes, point of sale devices, forecourt controllers, back office systems, fuel dispensers, etc.) disposed in the fuel storage facility can sense fuel data of the fuel storage facility. The fuel data can include any type of measurement data characterizing one or more aspects of the fuel storage facility including, for example, fuel tank levels, water content, leak detection, flow readings, equipment status, and so on.

At step 310, a wetstock management server communicatively coupled to the plurality of sensors can collect the acquired fuel data, via data processing unit 121, and process the fuel data to detect whether the fuel data satisfies an exception indicative of an operational issue of the fuel storage facility based on one or more predefined rules or models stored in the wetstock management server, via algorithms unit 122 and exceptions and services unit 123. The wetstock management server can be a remote, i.e., cloud-based, server located outside of the fuel storage facility. In some embodiments, the measured fuel data can be collected by a fuel data collection device (not shown), such as an IoT device, located on-site, and the fuel data collection device can transmit the collected data to the wetstock management server for processing.

Upon detecting that the collected fuel data satisfies an exception, the procedure 300 can proceed toward one or more outputs including generating and displaying a workflow (steps 315 through 325) and identifying a risk category and transmitting an alert via select communication channels (steps 330 through 340). In some embodiments, only one of the outputs can be carried out. In other embodiments, both outputs, or any combination thereof, can be carried out.

At step 315, the operational issue of the fuel storage facility can be identified based on the exception. For instance, if the exception derives from a sudden decrease in a fuel tank level, the operational issue can be identified as a fuel loss or leak.

At step 320, a workflow can be generated, via workflow unit 125, for assisting a user of the fuel storage facility to resolve the operational issue identified in step 315. The workflow can include a series of steps providing end-to-end support for the user to resolve the operational issue in the most appropriate and efficient manner. The workflow can be generated dynamically, that is, in real-time, taking into account on-site equipment and the seriousness of the issue.

At step 325, a device communicatively coupled to the wetstock management server can display a visual characterization of the workflow, such as a listing of the workflow steps. The device, e.g., a computer, a mobile device, a tablet, or the like, can include a display unit configured to display the visual characterization of the workflow. In some embodiments, the user can interact with the device by, for example, indicating through the device that a workflow step has been completed, that additional assistance is necessary, or the like.

Meanwhile, at step 330, a risk category among a plurality of predefined risk categories can be assigned to the exception, via risk escalation unit 124. Identifying the risk category can be carried out based on one or more exception criteria associated with each of the plurality of predefined risk categories. For example, as shown in Table 1, criteria relating to an amount by which fuel exceeds a predefined maximum limit can correspond to each risk category. The exception detected in step 310 can be compared with the exception criteria to assign the appropriate risk category to the exception.

At step 335, one or more electronic communication channels among a plurality of predefined electronic communication channels can be selected for transmission of an alert characterizing the operational issue to the user. Referring again to Table 1, each of the predefined risk categories can correspond to a particular set of electronic communication channels. Thus, the one or more electronic communication channels can be selected based on the assigned risk category.

At step 340, an alert or notification characterizing the operational issue can be electronically transmitted to the user, via notifications unit 126, using the one or more electronic communication channels selected in step 335. The number of users receiving the alert can depend upon the degree of urgency associated with the assigned risk category as well as the date and time at which the exception is detected. Also, the alert can be created and transmitted such that users are alerted only to on-site equipment issues when certain rules and/or risks are breached.

The procedure 300 can continue throughout operation of the fuel storage facility. The techniques by which the steps of procedure 300 may be performed, as well as ancillary procedures and exception criteria, are described in detail above.

It should be noted that the steps shown in FIG. 3 are merely examples for illustration, and certain other steps may be included or excluded as desired. Further, while a particular order of the steps is shown, this ordering is merely illustrative, and any suitable arrangement of the steps may be utilized without departing from the scope of the embodiments herein. Even further, the illustrated steps may be modified in any suitable manner in accordance with the scope of the present claims.

Accordingly, the automated wetstock management system as discussed herein can combine all known alerts and data points, site equipment, and infrastructure details into a model to provide a user with the most likely on-site fault based on both risk, likelihood, real-life probability, and the equipment on-site. By applying artificial intelligence and machine learning techniques to wetstock management procedures, wetstock management can be performed more efficiently, thereby saving costs and improving safety.

It should be understood that terminology used herein is for the purpose of describing particular embodiments only and is not intended to be limiting of the disclosure. As used herein, the singular forms "a," "an," and "the" are intended to include the plural forms as well, unless the context clearly indicates otherwise. It will be further understood that the terms "comprises," "includes," or variations thereof, when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. The term "coupled" denotes a physical relationship between two components whereby the components are either directly connected to one another or indirectly connected via one or more intermediary components.

Approximating language, as used herein throughout the specification and claims, may be applied to modify any quantitative representation that could permissibly vary without resulting in a change in the basic function to which it is related. Accordingly, a value modified by a term or terms, such as "about," "approximately," and "substantially," are not to be limited to the precise value specified. In at least some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise.

Additionally, it is understood that one or more of the above methods, or aspects thereof, may be executed by at least one control unit. The term "control unit" may refer to a hardware device that includes a memory and a processor. The memory is configured to store program instructions, and the processor is specifically programmed to execute the program instructions to perform one or more processes which are described above. The control unit may control operation of units, modules, parts, devices, or the like, as described herein. Moreover, it is understood that the above methods may be executed by an apparatus, such as a wetstock management server, comprising the control unit in conjunction with one or more other components, as would be appreciated by a person of ordinary skill in the art.

The foregoing description has been directed to embodiments of the present disclosure. It will be apparent, however, that other variations and modifications may be made to the described embodiments, with the attainment of some or all of their advantages. Accordingly, this description is to be taken only by way of example and not to otherwise limit the scope of the embodiments herein. Therefore, it is the object of the appended claims to cover all such variations and modifications as come within the true spirit and scope of the embodiments herein.

What is claimed is:

1. A method for automated wetstock management, comprising:
   receiving fuel data from one or more sensors disposed in a fuel storage facility, the fuel data characterizing one or more aspects of the fuel storage facility;
   determining, by a wetstock management server communicatively coupled to the plurality of sensors and using one or more predefined algorithms stored in the wetstock management server, whether the received fuel data satisfies one or more exceptions indicating one or more operational issues of the fuel storage facility;

determining, upon determination that the received fuel data satisfies the one or more exceptions and by the wetstock management server, a risk category to each of the one or more exceptions indicating a degree of risk;

generating, by the wetstock management server, a workflow in response to the satisfying of the one or more exceptions and the determining of the risk category, the generated workflow including one or more instructional steps to be performed by a user to resolve the one or more operational issues, the workflow being generated at least partially based upon stored data characterizing prior generated workflows to resolve past operational issues of the fuel storage facility; and providing graphical data characterizing the generated workflow to a display in electronic communication with the wetstock management server.

2. The method of claim 1, further comprising, upon resolution of the one or more operational issues and by the wetstock management server, updating the stored data with data characterizing the implementation of the generated workflow.

3. The method of claim 2, further comprising training, by the wetstock management server, one or more machine learning algorithms with the updated stored data.

4. The method of claim 1, further comprising notifying, by the wetstock management server, a user of the one or more exceptions via one or more modes of electronic communication.

5. The method of claim 4, wherein the one or more modes of electronic communication are determined based on the determined risk category.

6. The method of claim 4, wherein the one or more modes include displaying the generated workflow on an interactive computer application.

7. The method of claim 1, further comprising:
determining, by the wetstock management server, one or more causes of each of the one or more exceptions;
generating, by the wetstock management server, a confidence prediction for each of the one or more causes; and
providing, by the wetstock management server, the generated confidence prediction to the user.

8. The method of claim 7, wherein the workflow is generated at least partially based on the generated confidence prediction.

9. A method for automated wetstock management, comprising:
receiving fuel data from one or more sensors disposed in a fuel storage facility, the fuel data characterizing one or more aspects of the fuel storage facility;
determining, by a wetstock management server communicatively coupled to the plurality of sensors and using one or more predefined algorithms stored in the wetstock management server, whether the received fuel data satisfies one or more exceptions indicating one or more operational issues of the fuel storage facility;

assigning, upon determination that the received fuel data satisfies the one or more exceptions and by the wetstock management server, a risk category to each of the one or more exceptions indicating a degree of risk;

generating, using a machine learning algorithm trained on data collected from the fuel storage facility and by the wetstock management server, a workflow in response to the satisfying of the one or more exceptions and the assigning of the risk category, the generated workflow including one or more instructional steps to be performed by a user to resolve the one or more operational issues; and providing graphical data characterizing the generated workflow to a display in electronic communication with the wetstock management server.

10. The method of claim 9, wherein the determining is at least partially based on data characterizing prior operational issues of the fuel storage facility.

11. The method of claim 9, further comprising reassigning, upon resolution of the one or more operational issues and by the wetstock server, the assigned risk category to a lesser risk category.

12. The method of claim 11, receiving, upon resolution of the one or more operational issues, additional fuel data to ensure the one or more exceptions are no longer present.

13. The method of claim 9, further comprising examining, by the wetstock management server and with a machine learning based-system, the one or more steps as they are carried out to address the one or more operational issues in real-time to determine a response time.

14. The method of claim 13, further comprising:
comparing, by the wetstock management server, the response time against past resolution of one or more prior operational issues, and
determining, by the wetstock management server, an effectiveness of the one or more steps based on the comparison of the response time against the past resolution of the one or more prior operational issues.

15. The method of claim 9, further comprising:
receiving additional fuel data;
determining, by the wetstock management server, that the received additional fuel data satisfies one or more exceptions indicating an exacerbation of the one or more operational issues; and
invoking, using machine-learning techniques trained on the past resolution of one or more prior operational issues and by the wetstock management server, one or more automated reactions to the exacerbation.

* * * * *